United States Patent
Barbu et al.

(10) Patent No.: US 8,050,482 B2
(45) Date of Patent: **\*Nov. 1, 2011**

(54) SYSTEM AND METHOD FOR ONLINE OPTIMIZATION OF GUIDEWIRE VISIBILITY IN FLUOROSCOPIC SYSTEMS

(75) Inventors: Adrian Barbu, Tallahassee, FL (US); Vassilis Athitsos, Arlington, TX (US); Bogdan Georgescu, Plainsboro, NJ (US); Peter Durlak, Erlangen (DE); Dorin Comaniciu, Princeton Junction, NJ (US)

(73) Assignee: Siemens Medical Solutions USA, Inc., Malvern, PA (US)

(\*) Notice: Subject to any disclaimer, the term of this patent is extended or adjusted under 35 U.S.C. 154(b) by 1028 days.

This patent is subject to a terminal disclaimer.

(21) Appl. No.: 11/860,588

(22) Filed: Sep. 25, 2007

(65) Prior Publication Data
US 2008/0080754 A1     Apr. 3, 2008

Related U.S. Application Data

(60) Provisional application No. 60/827,236, filed on Sep. 28, 2006.

(51) Int. Cl.
*G06K 9/00*     (2006.01)

(52) U.S. Cl. .............................. 382/132; 382/128
(58) Field of Classification Search .............. None
See application file for complete search history.

(56) References Cited

U.S. PATENT DOCUMENTS

2006/0187462 A1\* 8/2006 Srinivasan et al. ............ 356/479
2008/0107314 A1\* 5/2008 Georgescu et al. ............ 382/128

OTHER PUBLICATIONS

Comaniciu, Dorin et al., "Dissimilarity Computation Through Low Rank Corrections," *Pattern Recognition Letters*, (2003) pp. 227-236.

\* cited by examiner

*Primary Examiner* — Brian Werner
*Assistant Examiner* — Nirav G Patel (57) ABSTRACT

A method for online optimization of guidewire visibility in fluoroscopic images includes providing an digitized image acquired from a fluoroscopic imaging system, the image comprising an array of intensities corresponding to a 2-dimensional grid of pixels, detecting a guidewire in the fluoroscopic image, enhancing the visibility of the guidewire in the fluoroscopic image, calculating a visibility measure of the guidewire in the fluoroscopic image, and readjusting acquisition parameters of the fluoroscopic imaging system wherein the guidewire visibility is improved.

18 Claims, 4 Drawing Sheets

SYSTEM AND METHOD FOR ONLINE OPTIMIZATION OF GUIDEWIRE VISIBILITY IN FLUOROSCOPIC SYSTEMS

CROSS REFERENCE TO RELATED UNITED STATES APPLICATIONS

This application claims priority from "Online Optimization of Guidewire Visibility in AX Systems", U.S. Provisional Application No. 60/827,236 of Athitsos, et al., filed Sep. 28, 2006, the contents of which are herein incorporated by reference.

TECHNICAL FIELD

This disclosure is directed to enhancing guidewire visibility in coronary angioplasty.

DISCUSSION OF THE RELATED ART

Coronary angioplasty is a medical procedure used to restore blood flow through clogged coronary arteries. During that procedure, a catheter is inserted through an artery in the thigh, and guided by a physician until it reaches the location of obstruction. Then, a guidewire is inserted inside the catheter through and beyond the obstruction. Over the guidewire, a catheter with a deflated balloon is inserted and guided so that the balloon reaches the blockage. At that point, the balloon is inflated and deflated several times so as to unblock the artery. A device called a stent is often placed at that position in order to keep the artery from becoming clogged again.

Figure 1:
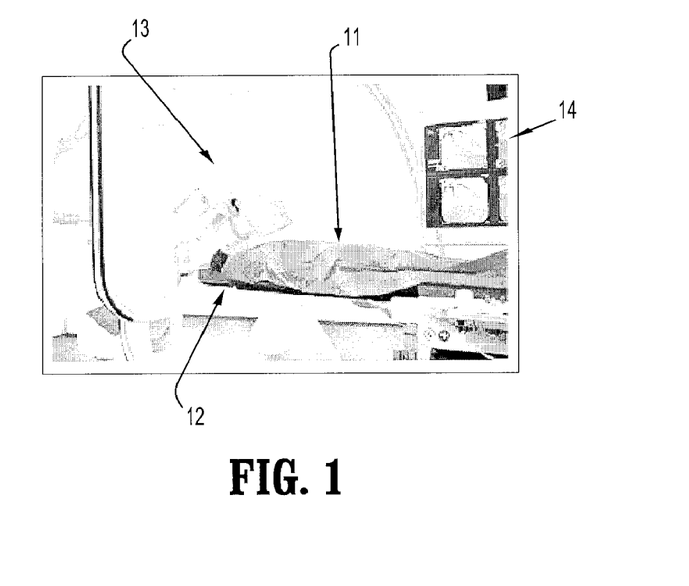
FIG. 1 depicts an exemplary fluoroscopy system in operation, according to an embodiment of the invention.
Figure 2:
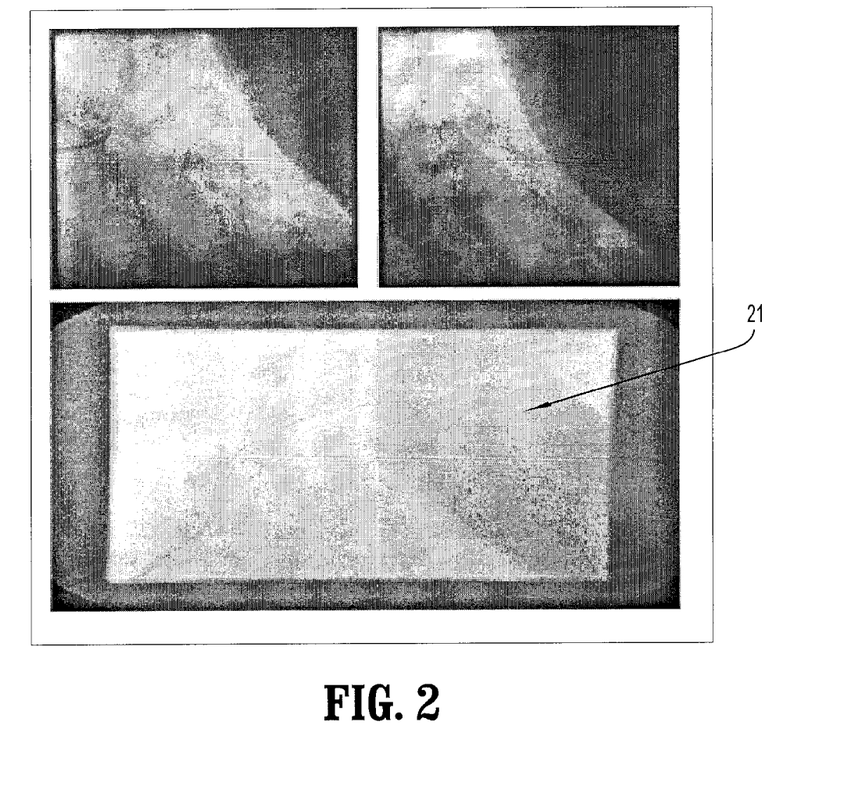
FIG. 2 presents some example images acquired using an exemplary fluoroscopy system, according to an embodiment of the invention.

Throughout this procedure, the physician uses fluoroscopic images in order to monitor the position of the catheter, the guidewire, the balloon, and the stent. Fluoroscopic images are X-ray images collected at a rate of several frames per second. In order to reduce the patient's exposure to X-ray radiation, the X-ray dosage is kept low and as a result the images tend to have low contrast and include a large amount of noise. An example of a fluoroscopy system in operation is shown in FIG. 1, with a patient 11 shown on an operating table 12 with flouroscopic camera 13 and display monitors 14. FIG. 2 presents some example images acquired using such a system. A guidewire 21 is indicated for the lower image in the figure. As can be seen in FIG. 2, it is often challenging to distinguish the objects of interest, in particular the catheter and guidewire, in such images. Tuning acquisition parameters so as to optimize the visibility of the guidewire can help physicians navigate the wire and stent through the arterial system during intervention, while minimizing the exposure of the patient to X-ray radiation. In addition, improving the visibility of the guidewire can make it easier to automatically detect the catheter and guidewire using specialized software.

Performing exhaustive search for guidewire detection and tracking in fluoroscopic images can be performed significantly faster in half-resolution or quarter-resolution. However, the guidewire is a very thin structure (typically about 2-3 pixels wide) even in the full-resolution images. Straightforward subsampling methods essentially blend guidewire pixels with the background, thus rendering the guidewire barely, if at all, visible in the downsampled images. As a result, detecting and tracking the guidewire in reduced resolution can become extremely challenging or even infeasible.

SUMMARY OF THE INVENTION

Exemplary embodiments of the invention as described herein generally include methods and systems for online optimization of image quality and guidewire visibility in fluoroscopic systems during medical intervention. The visibility of the guidewire is quantified based on the difference between the intensity/color distribution of that wire and the corresponding distribution of the background. Using an automatic detector/tracker to locate the guidewire, the guidewire visibility is measured online, and data acquisition parameters are automatically modified so as to improve the visibility.

According to an aspect of the invention, there is provided a method for online optimization of guidewire visibility in fluoroscopic images, the method including providing a digitized image acquired from a fluoroscopic imaging system, said image comprising an array of intensities corresponding to a 2-dimensional grid of pixels, detecting a guidewire in said fluoroscopic image, enhancing the visibility of the guidewire in said fluoroscopic image, calculating a visibility measure of said guidewire in said fluoroscopic image, and readjusting acquisition parameters of said fluoroscopic imaging system wherein said guidewire visibility is improved.

According to a further aspect of the invention, detecting a guidewire comprises filtering said image with one or more steerable filters of different angular orientations, assigning a weight W and orientation O for each pixel based on said filter response for each pixel, wherein each pixel weight is assigned to a function of a maximum filter response magnitude and said pixel orientation is calculated from the angle producing said maximum filter response if said magnitude is greater than zero, wherein guidewire pixels have a higher weight than non-guidewire pixels.

According to a further aspect of the invention, enhancing guidewire visibility comprises constructing a mask image $I_M$ wherein pixels that have high filter response and are close to said guidewire are also given value 1 and value 0 elsewhere, blurring said mask $I_M$ over every 3×3 pixel neighborhood, and multiplying the blurred mask by $0.1 \times (\max(I) - \min(I))$ and subtracting the result from said fluoroscopic image.

According to a further aspect of the invention, blurring said mask over a 3×3 pixel neighborhood comprises multiplying 3×3 sub-matrices of said mask by the following 3×3 matrix:

$$\begin{bmatrix} 0.0625 & 0.1250 & 0.0625 \\ 0.1250 & 0.2500 & 0.1250 \\ 0.0625 & 0.1250 & 0.0625 \end{bmatrix}$$

According to a further aspect of the invention, calculating a visibility measure comprises selecting a set of pixels on said guidewire, selecting a set of background pixels in a neighborhood of said guidewire that do not include the guidewire pixels, calculating a mean intensity $\mu_N$, $\mu_B$, and intensity variance $\sigma_N$, $\sigma_B$ for both the guidewire pixels and the background pixels, respectively, calculating a distance measure $d^2$ between said 2 sets of pixels as $$d^2(w) = \frac{1}{4}(\sigma_N - \sigma_B)^2(\sigma_N + \sigma_B)^{-1} + \frac{1}{2}\log\frac{\frac{1}{2}(\sigma_N + \sigma_B)}{\sqrt{\sigma_N \sigma_B}},$$

wherein w represents the guidewire pixels, and calculating a visibility V of said guidewire from $$V = \frac{1}{n}\sum_{i=1}^{n} d^2(w_i),$$

wherein the sum is over the guidewire pixels.

According to a further aspect of the invention, the method includes adding a contrast term $\epsilon$ to said distance measure, wherein $$d^2(w) = \frac{1}{4}(\mu_N - \mu_B)^2(\sigma_N + \sigma_B + \varepsilon)^{-1} + \frac{1}{2}\log\frac{\frac{1}{2}(\sigma_N + \sigma_B)}{\sqrt{\sigma_N \sigma_B}},$$

wherein a relative importance of the two terms is tuned by a value of said $\epsilon$-term.

According to a further aspect of the invention, calculating a distance measure between said 2 sets of pixels comprises normalizing the fluoroscopic image to take on values in the range from 0 to 1, blurring said image with a Gaussian to remove high frequency noise, computing a pixel value vector for the guidewire for a sequence of windows centered about and normal to the guidewire, averaged over a wire width, computing pixel value vectors for backgrounds $b_0$, $b_1$ on either side of the guidewire for said sequence of windows, averaged over background widths, calculating the mean vectors $\mu_N$, $\mu_{b_0}$, $\mu_{b_1}$ as a moving average of the moving window, and calculating the variances $\sigma_N$, $\sigma_B$ from the foreground and background means, and calculating the distance from $$d^2(w) = \frac{1}{8n}\sum_{i=1}^{n}\left[(\mu_N^i - \mu_{b0}^i)^2 + (\mu_N^i - \mu_{b1}^i)^2\right](\sigma_N + \sigma_B + \varepsilon)^{-1} + \frac{1}{2}\log\frac{\frac{1}{2}(\sigma_N + \sigma_B)}{\sqrt{\sigma_N \sigma_B}}$$

wherein the sum is over the sequence of windows, and n is the number of windows.

According to another aspect of the invention, there is provided a program storage device readable by a computer, tangibly embodying a program of instructions executable by the computer to perform the method steps for online optimization of guidewire visibility in fluoroscopic images.

DETAILED DESCRIPTION OF EXEMPLARY EMBODIMENTS

Exemplary embodiments of the invention as described herein generally include systems and methods for enhancing guidewire visibility in coronary angioplasty. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A method according to an embodiment of the invention can improve the visibility of the guidewire during image acquisition by automatically tuning the parameters of the fluoroscopic acquisition system. In the description herein below, the letter P is used to denote a vector of acquisition parameters, and I(P, t) is defined to be the image obtained at time t using acquisition parameters P. It is assumed that there exists a function V(I, L) that provides a quantitative measure of the visibility of the guidewire in image I, given the knowledge that the wire is at location L of the image. In fluoroscopic sequences, the guidewire is essentially a one-dimensional (1D) structure, and the location L of the guidewire in an image I can be provided as a sequence of pixels: $L=(w_1, \ldots w_n)$, where n is the total number of wire pixels.

Figure 3:
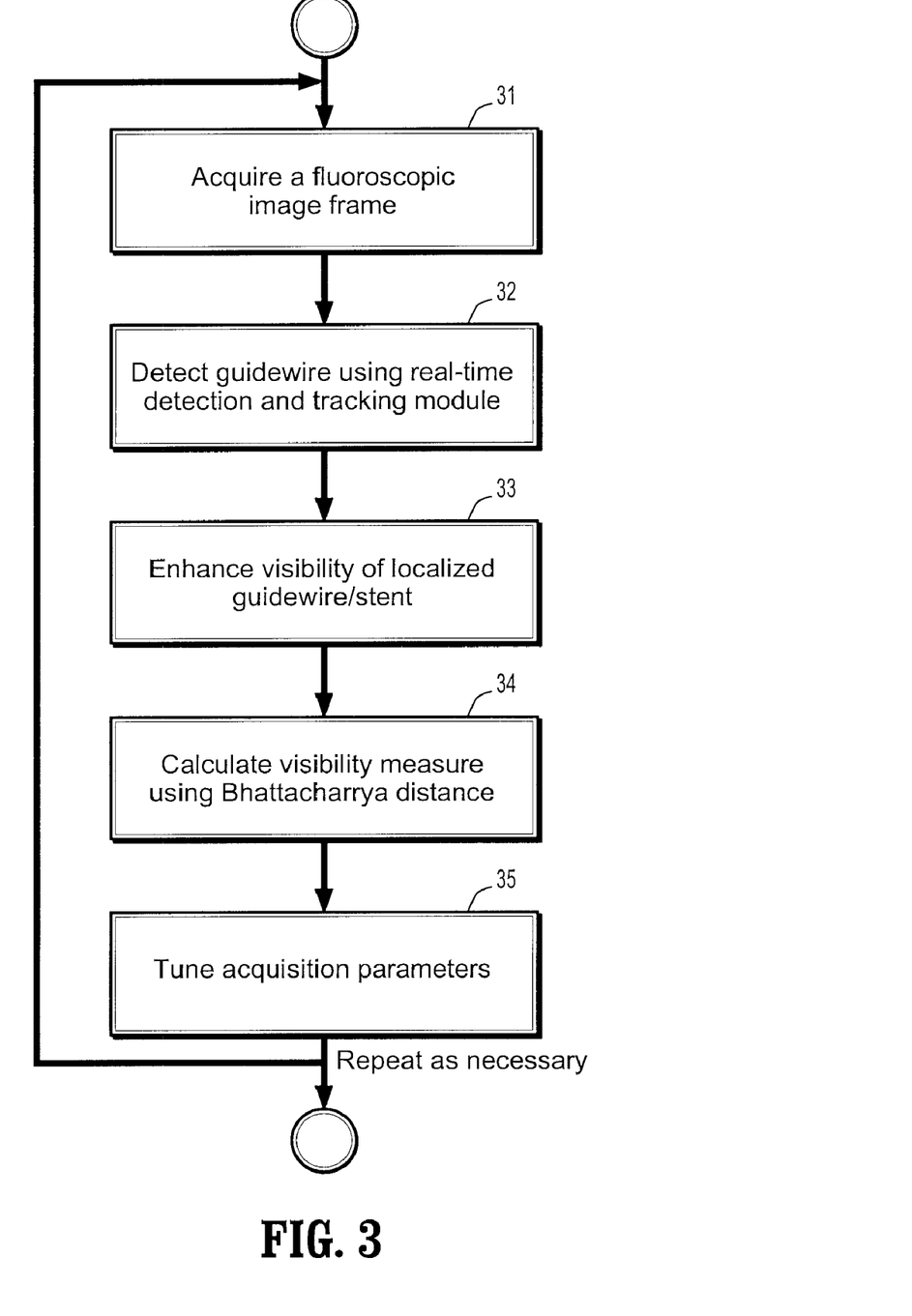
FIG. 3 is a flow chart of a control loop for automatic tuning of acquisition parameters to optimize guidewire visibility, according to an embodiment of the invention.

FIG. 3 is a flow chart of a control loop for enhancing guidewire visibility in coronary angioplasty, the control loop including acquiring an image frame, automatically detecting the guidewire, optionally enhancing the visibility of the guidewire in the image, measuring the visibility of the guidewire in the original or enhanced image, tuning the image acquisition parameters, and then proceeding to acquire the next frame. Referring now to the figure, a method begins art step 31 by the acquisition of a fluoroscopic image frame.

A real-time guidewire detection and tracking module is applied to the frame at step 32. According to an embodiment of the invention, the location L of the guidewire can be estimated automatically using an automatic guidewire detection/tracking module. According to another embodiment of the invention, an alternative to a fully automatic system is to have a human participate in the control loop, by either manually specifying the object location, or by correcting, when needed, the outcome of automatic detection/tracking.

Given the estimated location and the quantitative measure of visibility, the acquisition parameters of the fluoroscopic system can be adjusted so as to maximize the value of visibility score V. The acquisition parameters relate to any factors that influence the conversion of the signal up to the displayed image. For example, for digital conversion, the quantization range can be adapted to obtain a better resolution over a certain range. So, by knowing the guidewire location one knows the intensity range for the region-of-interest as well as where to measure visibility enhancement.

According to another embodiment of the invention, an optional step 33, after guidewire detection, is to apply a domain-specific enhancement algorithm to enhance the visibility of the guidewire. A guidewire enhancement method according to an embodiment of the invention proceeds as follows. First, the guidewire is detected using an automatic guidewire detection algorithm. A mask image $I_M$ is constructed with value 1 at all detected guidewire pixels and value 0 elsewhere. A Gaussian-derivative steerable filter is applied to the original input image I. A peak non-zero pixel response magnitude to the filter for a given angle is indicative of the presence of a guidewire oriented at the given angle. The pixels that have high filter response and are close to the guidewire are also given value 1. According to an exemplary, non-limiting embodiment of the invention, close is defined as a distance at most I pixel from the guidewire. This step makes sure that the mask has the width of the wire, in case the wire is thicker than 1 pixel and it is clearly visible. The matrix $I_M$ is slightly blurred by weighting each pixel over its 3×3 neighborhood to reduce aliasing:

$$I'_M = I_M \cdot \begin{bmatrix} 0.0625 & 0.1250 & 0.0625 \\ 0.1250 & 0.2500 & 0.1250 \\ 0.0625 & 0.1250 & 0.0625 \end{bmatrix} \quad (1)$$

This 3×3 neighborhood is exemplary and non-limiting, and other 3×3 weighting matrices, and different size neighborhoods, such as a 2×2 neighborhood, can be similarly defined in other embodiments of the invention. The resulting mask $I_M'$ multiplied by 0.1(max(I)−min(I)) is subtracted from the intensity image I:

$$I' = I - I_M' \cdot 0.1(\max(I) - \min(I)) \quad (2)$$

Then, the visibility measure disclosed below in EQ. (8) can be applied to the enhanced image I', as opposed to the original image I.

Additional methods for detecting and tracking a guidewire and enhancing guidewire visibility during coronary angioplasty are disclosed in these inventors' copending patent application. "A Method for Simultaneously Subsampling Fluoroscopic Images and Enhancing Guidewire Visibility", Siemens Docket No. 2006P20839US01, filed concurrently, the contents of which are herein incorporated by reference in their entirety.

At step 34, the visibility of the guidewire is measured. Intuitively, in order for the wire to be highly visible, wire pixels should be darker than their adjacent background pixels. Given an individual guidewire pixel w, its visibility can be measured using the Bhattacharyya distance between the distribution of intensities in wire pixels close to w and the distribution of intensities in back-round pixels close to w. The Bhattacharyya distance allows a compact feature representation and an efficient dissimilarity computation. In its general form, the Bhattacharyya distance between two arbitrary distributions $\{p_i(x)\}_{i=1,2}$ is defined as $$d_B^2 = -\log\int\sqrt{p_1(x)p_2(x)}dx. \quad (3)$$

Although not a metric, as it does not obey the triangle inequality, this distance is useful in classification problems since it is closely related to the Bayes error, and has a well defined geometric interpretation, relation to the Fisher measure of information, statistical properties of the sample estimates, and explicit forms for various distributions.

A motivation to use the Bhattacharyya distance is based on its relationship to the Jensen-Shannon divergence based statistical test of the homogeneity between two distributions, $$JS(p_1, p_2) = \int p_1(x)\log\frac{p_1(x)}{(p_1(x)+p_2(x))/2}dx + \int p_2(x)\log\frac{p_2(x)}{(p_1(x)+p_2(x))/2}dx. \quad (4)$$

It can be shown that if the two distributions are normal, the Jensen-Shannon divergence reduces to the Bhattacharyya distance (up to a constant). Thus, the similarity can be formulated as a goodness-of-.t test between the empirical distributions $p_1$ and $p_2$ and the homogeneous model $(p_1+p_2)/2$ A comparative study of similarity measures found the Jensen-Shannon divergence superior to the Cramer-von Mises and Kolmogorov-Smirnov statistical tests. The Jensen-Shannon divergence has also been used for texture classification. A more recent study shows that most of these similarity functions are related to the Bayesian criterion.

Other measures such as the Fisher linear discriminant function yield useful results only when the two distributions have different means, whereas the Kullback divergence provides in various instances lower performance than the Bhattacharyya distance. The Bhattacharyya distance is a particular case of the Chernoff distance. While the latter in general provides a better bound for the Bayesian error, it is more difficult to evaluate. The Chernoff and Bhattacharyya bounds have been used recently to analyze the performance of edge detectors.

The expression of EQ. (3) is defined for arbitrary distributions, however, it will be assumed herein that the distribution of the feature of interest is unimodal, characterized by its mean vector $\mu \in R^p$ and covariance matrix $C \in R^{p \times p}$. This is equivalent to describing each image as homogeneous relative to the feature under consideration. When the feature distribution is a multivariate normal, the mean vector and covariance matrix uniquely define it, otherwise they provide an incomplete but most often satisfactory representation.

For two p-dimensional normal distributions characterized by $\mu_1$, $C_1$ and $\mu_2$, $C_2$, the Bhattacharyya distance of EQ. (3) becomes $$d_B^2 = \frac{1}{4}(\mu_1 - \mu_2)^T(C_1 + C_2)^{-1}(\mu_1 - \mu_2) + \frac{1}{2}\log\frac{\left|\frac{C_1+C_2}{2}\right|}{\sqrt{|C_1||C_2|}}, \quad (5)$$

where $||$ is the determinant and T is the transpose operator. The first term provides the class separability due to the mean-difference, while the second term provides class separability due to the covariance-difference.

Let N(w) be the wire pixels close to w, and B(w) be the background pixels close to w, where "close" can be defined as "within distance d from w." Assuming that the intensities of pixels in N(w) and B(w) follow a normal distribution, then let $\mu_N$, $\sigma_N$ be the mean and variance of the intensity values in N(w) and $\mu_B$, $\sigma_B$ be the mean and variance for the intensity values in B(w). Then, the Bhattacharyya distance $d^2(w)$ between the two distributions around pixel w is:

$$d^2(w) = \frac{1}{4}(\mu_N - \mu_B)^2(\sigma_N + \sigma_B)^{-1} + \frac{1}{2}\log\frac{\frac{1}{2}(\sigma_N + \sigma_B)}{\sqrt{\sigma_N \sigma_B}}. \quad (6)$$

According to another embodiment of the invention, the Bhattacharyya distance can be modified with the addition of a contrast term $\epsilon$:

$$d^2(w) = \frac{1}{4}(\mu_N - \mu_B)^2(\sigma_N + \sigma_B + \varepsilon)^{-1} + \frac{1}{2}\log\frac{\frac{1}{2}(\sigma_N + \sigma_B)}{\sqrt{\sigma_N \sigma_B}}. \quad (7)$$

The $\epsilon$ term allows one to tune the relative importance of the two terms in the above equation and to increase the importance of the contrast (the difference between background and foreground).

The visibility of the entire guidewire, $V(I, (w_1, \ldots, w_n))$, is defined as the average of the $d^2(w)$ values for wire pixels:

$$V(I, (w_1, \ldots, w_n)) = \frac{1}{n}\sum_{i=1}^{n} d^2(w_i). \quad (8)$$

According to an embodiment of the invention, an exemplary, non-limiting N(w) is defined as follows: take, along the wire curve, a curve segment that is 21 pixels long such that the center pixel (the $11^{th}$ pixel) is w. The set N(w) comprises those 21 pixels. The set B(w) of background pixels is constructed as follows: For each pixel p' along that curve, include in B(w) the two pixels that, when the curve is oriented to be horizontal at p', are above and below p' and at distance of 2 pixels from p'. When the curve orientation at p' is not horizontal, the coordinates of those two pixels are not integer coordinates. In that case, the intensity at those pixels is computed using bilinear interpolation. Note that the numeric values for the curve segment length and the width of the background are illustrative, and other values can be used as necessary to define the sets N(w) and B(w) according to other embodiments of the invention.

According to an embodiment of the invention, the Bhattacharyya distance can be implemented as follows. First, the input image is normalized to take on values in the range from 0 to 1. Then, the image is blurred with a Gaussian to remove high frequency noise. An exemplary, non-limiting variance for said Gaussian is 2 pixels. The pixel value vector for the guidewire is computed for a sequence of windows centered about and normal to the guidewire, averaged over the wire width. An exemplary, non-limiting wire width value according to an embodiment of the invention is 2 pixels. Pixel value vectors for the backgrounds $b_0$, $b_1$ on either side of the wire are also computed, averaged over the background widths. An exemplary, non-limiting background width value according to an embodiment of the invention is 3 pixels. The contrast term $\epsilon$ is initially set to 0.002. To accommodate a changing intensity along the guidewire, the mean vectors $\mu_N, \mu_{b_0}, \mu_{b_1}$ are calculated as a moving average of the moving window, and the variances $\sigma_N, \sigma_B$ are calculated front the foreground and background means. To calculate the Bhattacharyya distance, the $(\mu_N - \mu_B)^2$ term is replaced with $$\frac{1}{2n}\sum_{i=1}^{n}[(\mu_N^i - \mu_{b0}^i)^2 + (\mu_N^i - \mu_{b1}^i)^2]$$

where the sum is over the sequence of windows, and n is the number of windows. The distance measure then becomes $$d^2(w) =$$
$$\frac{1}{8n}\sum_{i=1}^{n}[(\mu_N^i - \mu_{b0}^i)^2 + (\mu_N^i - \mu_{b1}^i)^2](\sigma_N + \sigma_B + \varepsilon)^{-1} + \frac{1}{2}\log\frac{\frac{1}{2}(\sigma_N + \sigma_B)}{\sqrt{\sigma_N \sigma_B}}.$$

Referring again to FIG. 3, at step 35, given the estimated location and the quantitative measure of visibility, the acquisition parameters of the fluoroscopic system can be adjusted so as to maximize the value of visibility score V. These adjusted parameters can be used for the acquisition of another fluoroscopic frame at step 31. The steps illustrated in connection with FIG. 3 can be repeated as necessary to refine the image acquisition process.

A method according to another embodiment of the invention can be extended to more general domains, with different types of acquisition systems and different objects of interest. What is needed is to provide an automatic detector/tracker for the object of interest, and a domain-specific measure for evaluating the visibility of the object of interest. Then, a control loop similar to that depicted in FIG. 3 can be applied, to optimize the acquisition parameters.

Figure 4:
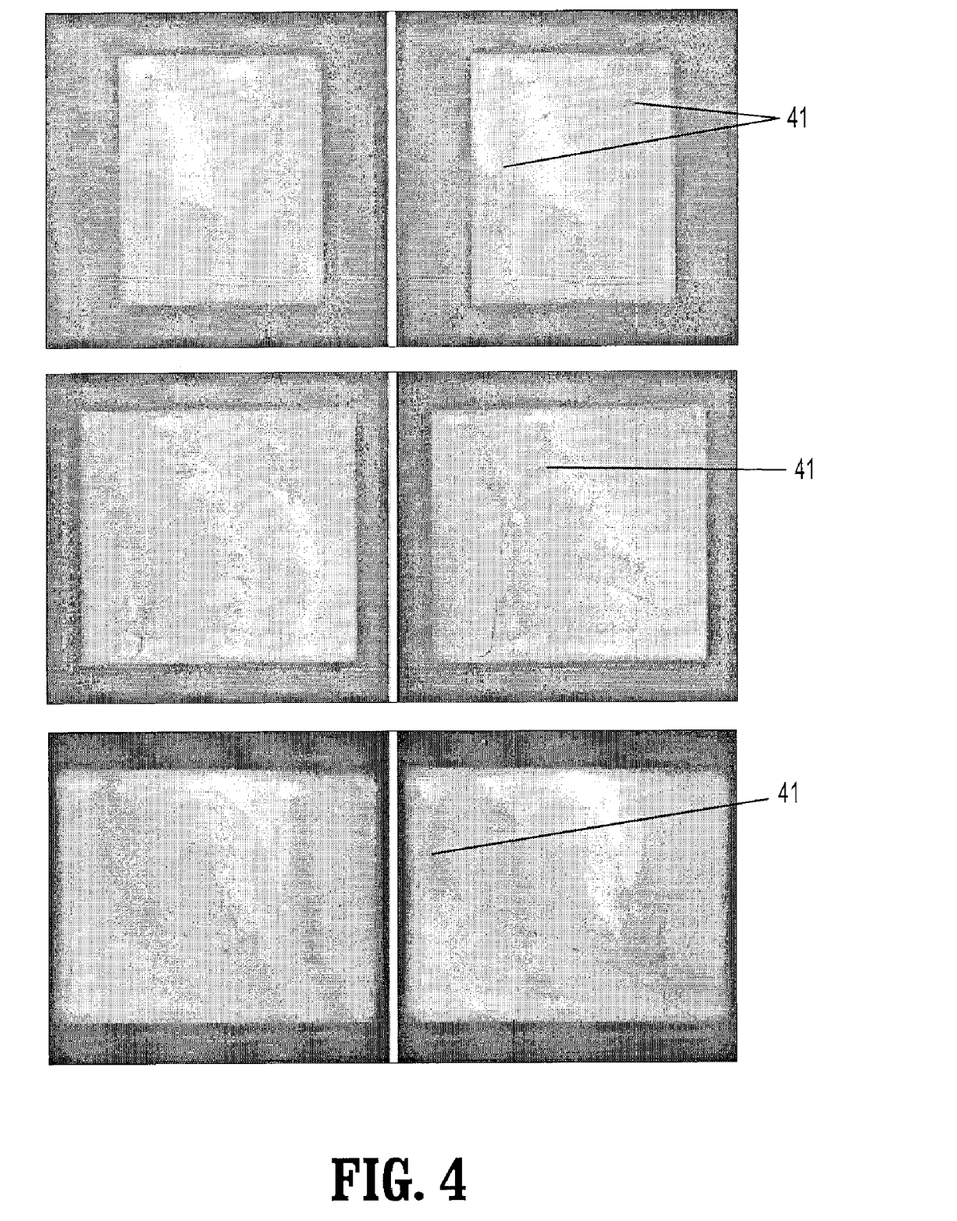
FIG. 4 depicts examples of enhancement results using guidewire detection in fluoroscopic image, according to an embodiment of the invention.

FIG. 4 depicts examples of enhancement results using guidewire detection in fluoroscopic image, according to an embodiment of the invention. The images on the left hand side are the original fluoroscopic images, while the images on the right depict the guidewire enhancement result. The guidewire in the enhanced images is indicated by reference number 41.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 5:
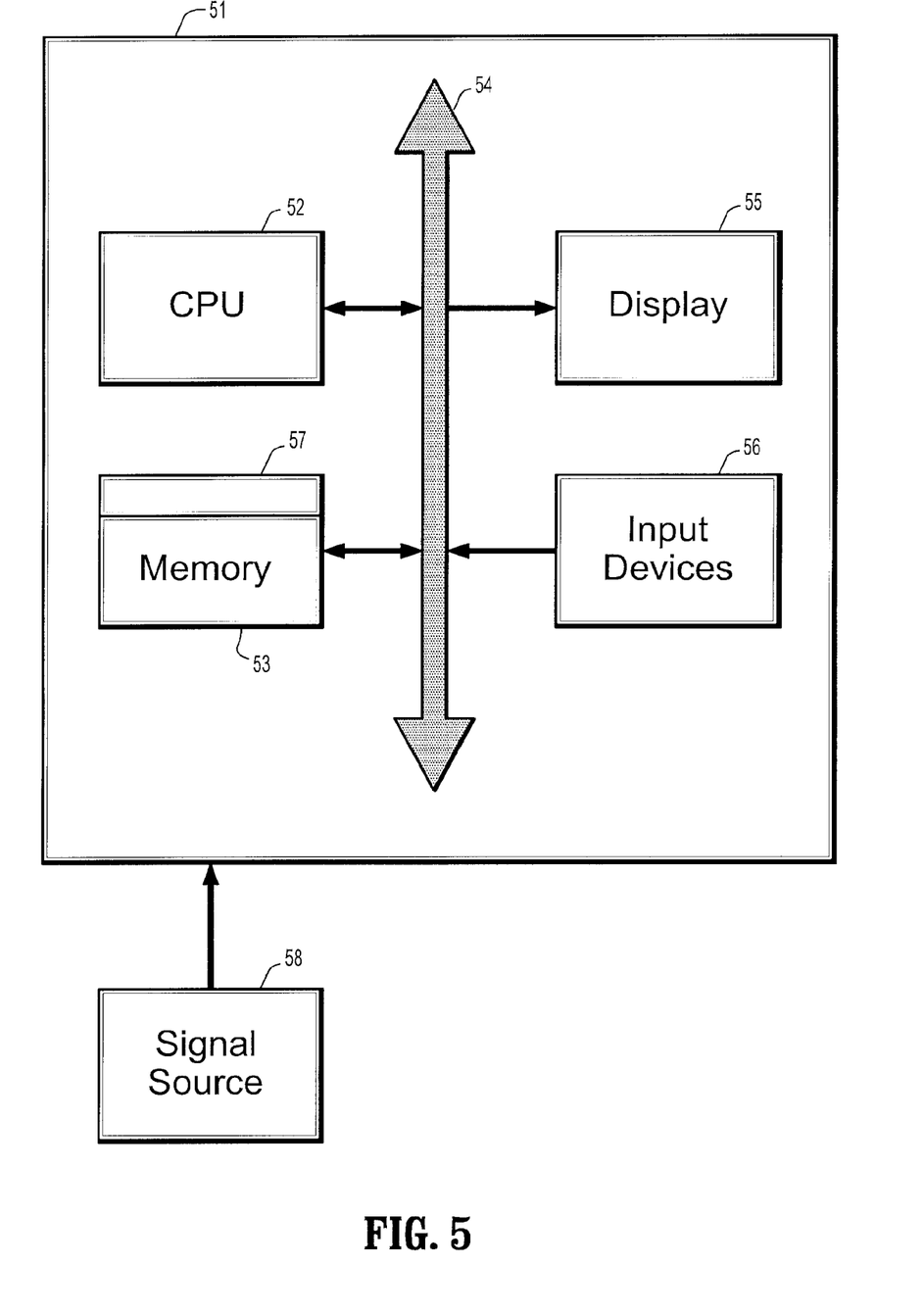
FIG. 5 is a block diagram of an exemplary computer system for implementing a control loop for automatic tuning of acquisition parameters to optimize guidewire visibility, according to an embodiment of the invention.

FIG. 5 is a block diagram of an exemplary computer system for implementing a method for enhancing guidewire visibility in coronary angioplasty according to an embodiment of the invention. Referring now to FIG. 5, a computer system 51 for implementing the present invention can comprise, inter alia, a central processing unit (CPU) 52, a memory 53 and an input/output (I/O) interface 54. The computer system 51 is generally coupled through the I/O interface 54 to a display 55 and various input devices 56 such as a mouse and a keyboard. The support circuits can include circuits such as cache, power supplies, clock circuits, and a communication bus. The memory 53 can include random access memory (RAM), read only memory (ROM), disk drive, tape drive, etc., or a combinations thereof. The present invention can be implemented as a routine 57 that is stored in memory 53 and executed by the CPU 52 to process the signal from the signal source 58. As such, the computer system 51 is a general purpose computer system that becomes a specific purpose computer system when executing the routine 57 of the present invention.

The computer system 51 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While embodiments of the present invention have been described in detail with reference to a preferred embodiment, those skilled in the art will appreciate that various modifications and substitutions can be made thereto without departing from the spirit and scope of the invention as set forth in the appended claims.

What is claimed is:

1. A method for online optimization of guidewire visibility in fluoroscopic images, comprising the steps of:
   providing an digitized image acquired from a fluoroscopic imaging system, said image comprising an array of intensities corresponding to a 2-dimensional grid of pixels;
   detecting a guidewire in said fluoroscopic image;
   enhancing the visibility of the guidewire in said fluoroscopic image;
   calculating a visibility measure of said guidewire in said fluoroscopic image; and
   readjusting acquisition parameters of said fluoroscopic imaging system wherein said guidewire visibility is improved,
   wherein enhancing guidewire visibility comprises constructing a mask image $I_M$ wherein pixels that have high filter response and are at most one pixel from said guidewire are also given value 1 and value 0 elsewhere, blurring said mask $I_M$ over every 3×3 pixel neighborhood, and multiplying the blurred mask by 0.1×(max(I)−min(I)) and subtracting the result from said fluoroscopic image.

2. The method of claim 1, wherein detecting a guidewire comprises filtering said image with one or more steerable filters of different angular orientations, assigning a weight W and orientation O for each pixel based on said filter response for each pixel, wherein each pixel weight is assigned to a function of a maximum filter response magnitude and said pixel orientation is calculated from the angle producing said maximum filter response if said magnitude is greater than zero, wherein guidewire pixels have a higher weight than non-guidewire pixels.

3. The method of claim 1, wherein blurring said mask over a 3×3 pixel neighborhood comprises multiplying 3×3 submatrices of said mask by the following 3×3 matrix:

$$\begin{bmatrix} 0.0625 & 0.1250 & 0.0625 \\ 0.1250 & 0.2500 & 0.1250 \\ 0.0625 & 0.1250 & 0.0625 \end{bmatrix}$$

4. The method of claim 1, wherein calculating a visibility measure comprises:
   selecting a set of pixels on said guidewire;
   selecting a set of background pixels in a neighborhood of said guidewire that do not include the guidewire pixels;
   calculating a mean intensity $\mu_N$, $\mu_B$, and intensity variance $\sigma_N$, $\sigma_B$ for both the guidewire pixels and the background pixels, respectively;
   calculating a distance measure $d^2$ between said 2 sets of pixels as $$d^2(w) = \frac{1}{4}(\sigma_N - \sigma_B)^2(\sigma_N + \sigma_B)^{-1} + \frac{1}{2}\log\frac{\frac{1}{2}(\sigma_N + \sigma_B)}{\sqrt{\sigma_N \sigma_B}},$$

wherein w represents the guidewire pixels; and
   calculating a visibility V of said guidewire from $$V = \frac{1}{n}\sum_{i=1}^{n} d^2(w_i),$$

wherein the sum is over the guidewire pixels.

5. The method of claim 4, further comprising adding a contrast term $\epsilon$ to said distance measure:

$$d^2(w) = \frac{1}{4}(\mu_N - \mu_B)^2(\sigma_N + \sigma_B + \varepsilon)^{-1} + \frac{1}{2}\log\frac{\frac{1}{2}(\sigma_N + \sigma_B)}{\sqrt{\sigma_N \sigma_B}}.$$

wherein a relative importance of the two terms is tuned by a value of said $\epsilon$-term.

6. A computer-implemented method for online optimization of guidewire visibility in fluoroscopic images, the method performed by a computer comprising the steps of:
   providing an digitized image acquired from a fluoroscopic imaging system, said image comprising an array of intensities corresponding to a 2-dimensional grid of pixels;
   detecting a guidewire in said fluoroscopic image;
   computing a pixel value vector for the guidewire for a sequence of windows centered about and normal to the guidewire, averaged over a wire width;
   computing pixel value vectors for backgrounds $b_0$, $b_1$ on either side of the guidewire for said sequence of windows, averaged over background widths;
   calculating mean vectors $\mu_N$, $\mu_{b_0}$, $\mu_{b_1}$ as a moving average of the moving window, and calculating variances $\sigma_N$, $\sigma_B$ from the foreground and background means; and
   calculating a distance between said guidewire pixels and said background pixels from $$d^2(w) = \frac{1}{8n}\sum_{i=1}^{n}\left[(\mu_N^i - \mu_{b0}^i)^2 + (\mu_N^i - \mu_{b1}^i)^2\right](\sigma_N + \sigma_B + \varepsilon)^{-1} + \frac{1}{2}\log\frac{\frac{1}{2}(\sigma_N + \sigma_B)}{\sqrt{\sigma_N \sigma_B}}$$

wherein w represents the guidewire pixels, the sum is over the sequence of windows, and n is the number of windows; and
   calculating a visibility V of said guidewire from $$V = \frac{1}{n}\sum_{i=1}^{n} d^2(w_i),$$

wherein the sum is over the guidewire pixels.

7. The method of claim 6, further comprising readjusting acquisition parameters of said fluoroscopic imaging system wherein said guidewire visibility is improved.

8. The method of claim 6, further comprising normalizing the fluroscopic image to take on values in the range from 0 to 1.

9. The method of claim 6, further comprising blurring said image with a Gaussian to remove high frequency noise.

10. The method of claim 6, further comprising constructing a mask image $I_M$ wherein pixels that have high filter response and are close to said guidewire are also given value 1 and value 0 elsewhere, blurring said mask $I_M$ over every 3×3 pixel neighborhood, and multiplying the blurred mask by 0.1× (max(I)−min(I)) and subtracting the result from said fluoroscopic image, wherein the visibility of the guidewire in said fluoroscopic image is enhanced.

11. The method of claim 6, further comprising adding a contrast term $\epsilon$ to the $(\sigma_N+\sigma_B)^{-1}$ factor of distance measure, wherein a relative importance of the two terms is tuned by a value of said $\epsilon$-term.

12. The method of claim 6, wherein calculating a distance measure between said 2 sets of pixels comprises:
normalizing the fluroscopic image to take on values in the range from 0 to 1;
blurring said image with a Gaussian to remove high frequency noise;
computing a pixel value vector for the guidewire for a sequence of windows centered about and normal to the guidewire, averaged over a wire width;
computing pixel value vectors for backgrounds $b_0$, $b_1$ on either side of the guidewire for said sequence of windows, averaged over background widths;
calculating the mean vectors $\mu_N$, $\mu_{b_0}$, $\mu_{b_1}$ as a moving average of the moving window, and calculating the variances $\sigma_N$, $\sigma_B$ from the foreground and background means; and
calculating the distance from $$d^2(w) = \frac{1}{8n}\sum_{i=1}^{n}\left[(\mu_N^i - \mu_{b0}^i)^2 + (\mu_N^i - \mu_{b1}^i)^2\right](\sigma_N + \sigma_B + \varepsilon)^{-1} + \frac{1}{2}\log\frac{\frac{1}{2}(\sigma_N + \sigma_B)}{\sqrt{\sigma_N\sigma_B}}$$

wherein the sum is over the sequence of windows, and n is the number of windows.

13. A program storage device readable by a computer, tangibly embodying a program of instructions executable by the computer to perform the method steps for online optimization of guidewire visibility in fluoroscopic images, said method comprising the steps of:
providing an digitized image acquired from a fluoroscopic imaging system, said image comprising an array of intensities corresponding to a 2-dimensional grid of pixels;
detecting a guidewire in said fluoroscopic image;
enhancing the visibility of the guidewire in said fluoroscopic image;
calculating a visibility measure of said guidewire in said fluoroscopic image; and
readjusting acquisition parameters of said fluoroscopic imaging system wherein said guidewire visibility is improved,
wherein enhancing guidewire visibility comprises constructing a mask image $I_M$ wherein pixels that have high filter response and are at most one pixel from said guidewire are also given value 1 and value 0 elsewhere, mask $I_M$ over every 3×3 pixel neighborhood, and multiplying the blurred mask by 0.1×(max(I)−min(I)) and subtracting the result from said fluoroscopic image.

14. The computer readable program storage device of claim 13, wherein detecting a guidewire comprises filtering said image with one or more steerable filters of different angular orientations, assigning a weight W and orientation O for each pixel based on said filter response for each pixel, wherein each pixel weight is assigned to a function of a maximum filter response magnitude and said pixel orientation is calculated from the angle producing said maximum filter response if said magnitude is greater than zero, wherein guidewire pixels have a higher weight than non-guidewire pixels.

15. The computer readable program storage device of claim 13, wherein blurring said mask over a 3×3 pixel neighborhood comprises multiplying 3×3 sub-matrices of said mask by the following 3×3 matrix:

$$\begin{bmatrix} 0.0625 & 0.1250 & 0.0625 \\ 0.1250 & 0.2500 & 0.1250 \\ 0.0625 & 0.1250 & 0.0625 \end{bmatrix}$$

16. The computer readable program storage device of claim 13, wherein calculating a visibility measure comprises:
selecting a set of pixels on said guidewire;
selecting a set of background pixels in a neighborhood of said guidewire that do not include the guidewire pixels;
calculating a mean intensity $\mu_N$, $\mu_B$, and intensity variance $\sigma_N$, $\sigma_B$ for both the guidewire pixels and the background pixels, respectively;
calculating a distance measure $d^2$ between said 2 sets of pixels as $$d^2(w) = \frac{1}{4}(\sigma_N - \sigma_B)^2(\sigma_N + \sigma_B)^{-1} + \frac{1}{2}\log\frac{\frac{1}{2}(\sigma_N + \sigma_B)}{\sqrt{\sigma_N\sigma_B}},$$

wherein w represents the guidewire pixels; and
calculating a visibility V of said guidewire from $$V = \frac{1}{n}\sum_{i=1}^{n} d^2(w_i),$$

wherein the sum is over the guidewire pixels.

17. The computer readable program storage device of claim 16, the method further comprising adding a contrast term $\epsilon$ to said distance measure:

$$d^2(w) = \frac{1}{4}(\mu_N - \mu_B)^2(\sigma_N + \sigma_B + \varepsilon)^{-1} + \frac{1}{2}\log\frac{\frac{1}{2}(\sigma_N + \sigma_B)}{\sqrt{\sigma_N\sigma_B}}.$$

wherein a relative importance of the two terms is tuned by a value of said $\epsilon$-term.

18. The computer readable program storage device of claim 17, wherein calculating a distance measure between said 2 sets of pixels comprises:
normalizing the fluroscopic image to take on values in the range from 0 to 1;

blurring said image with a Gaussian to remove high frequency noise;

computing a pixel value vector for the guidewire for a sequence of windows centered about and normal to the guidewire, averaged over a wire width;

computing pixel value vectors for backgrounds $b_0$, $b_1$ on either side of the guidewire for said sequence of windows, averaged over background widths;

calculating the mean vectors $\mu_N$, $\mu_{b_0}$, $\mu_{b_1}$ as a moving average of the moving window, and calculating the variances $\sigma_N$, $\sigma_B$ from the foreground and background means; and calculating the distance from $$d^2(w) = \frac{1}{8n}\sum_{i=1}^{n}[(\mu_N^i - \mu_{b0}^i)^2 + (\mu_N^i - \mu_{b1}^i)^2](\sigma_N + \sigma_B + \varepsilon)^{-1} + \frac{1}{2}\log\frac{\frac{1}{2}(\sigma_N + \sigma_B)}{\sqrt{\sigma_N \sigma_B}}$$

wherein the sum is over the sequence of windows, and n is the number of windows.

* * * * *